United States Patent [19]
Abela

[11] Patent Number: 5,330,467
[45] Date of Patent: * Jul. 19, 1994

[54] CELL TREATMENT APPARATUS AND METHOD

[76] Inventor: George S. Abela, 80 Longfellow Rd., Wellesley, Mass. 02181

[ * ] Notice: The portion of the term of this patent subsequent to Sep. 21, 2010 has been disclaimed.

[21] Appl. No.: 53,206

[22] Filed: Apr. 28, 1993

Related U.S. Application Data

[63] Continuation of Ser. No. 866,473, Apr. 10, 1992.

[51] Int. Cl.$^5$ ............................................. A61B 17/36
[52] U.S. Cl. ........................................ 606/15; 606/7; 606/13
[58] Field of Search ............................... 606/7, 13–16; 128/395–398; 607/88–89; 604/21

[56] References Cited

U.S. PATENT DOCUMENTS

| | | |
|---|---|---|
| Re. 31,815 | 1/1985 | Alfano . |
| 4,648,892 | 3/1987 | Kittrell et al. . |
| 4,686,979 | 8/1987 | Gruen et al. . |
| 4,748,980 | 6/1988 | Cremer et al. . |
| 4,785,806 | 11/1988 | Deckelbaum . |
| 4,860,743 | 8/1989 | Abela . |
| 4,913,142 | 4/1990 | Kittrell et al. ........................ 606/7 |
| 5,041,109 | 8/1991 | Abela . |
| 5,061,265 | 10/1991 | Abela et al. ......................... 606/15 |

OTHER PUBLICATIONS

Tao et al., "Direct Gene Transfer into Human Cultured Cells . . . " Jun. 1987, Pro Natl Acad Sci, vol. 84.
"The Perforated Balloon Catheter: Assessment and Minimization of Arterial Trauma", *JACC*, vol. 19, No. •3, Mar. 1, 1992, p. 107A Charles Lambert and Timothy Grady.
"High-Velocity Microprojectiles for Delivering Nucleic Acids Into Living Cells", T. M. Klein, E. D. wolf, R. Wu, & J. C. Sanford, *Letters to Nature*, vol. 327, May 7, 1987, pp. 70–73.
"Biolistic Transformation: Microbes to Mice", S. A. Johnston, *Nature*, vol. 346, Aug. 23, 1990, pp. 776–777.
"Gene Transfer Into Mammalian Cells By Rapid Freezing", Kiyoshi Sasaki et al, *In Vitro Cell. Dev. Biol. 27A:* pp. 86–88, Jan. 1991.
"High Efficiency Gene Transfection by Electroporation Using a Radio–Frequency Electric Field", Donald C. Chang et al, Biochimica et Biophysica Acta, 1992 (1991) pp. 153–160.
"Site Specific Gene Expression in Vivo by Direct Gene Transfer into the Arterial Wall", Elizabeth G. Nabel et al, *Science*, Sep. 14, 1990, pp. 1285–1288.
"Direct In Vivo Gene Transfer Into the Coronary and Peripheral Vasculatures of the Intact Dog", Chang S. Lim et al, *Circulation*, vol. 83, No. 6, Jun. 1991, pp. 2007–2011.
"Direct Gene Transfer Into Human Cultured Cells Facilitated by Laser Micropuncture of the Cell Membrane", Wen Tao et al, *Proc. Natl. Acam. Sci. USA*, vol. 84, pp. 4180–4184, Jun. 1987.
"The Laser Method for Efficient Introduction of Foreign DNA into Cultured Cells", Shun–ichi Kurata et al, *Experimental Cell Research 162*, (1986), pp. 372–378.
"Introduction of Foreign Genes Into Tissues of Living Mice by DNA–Coated Microprojectiles", R. Sanders Williams et al, *Proc. Natl. Acad. Sci. USA*, vol. 88, Apr. 1991, pp. 2726–2730, Genetics.

*Primary Examiner*—Stephen C. Pellegrino
*Assistant Examiner*—Michael Peffley
*Attorney, Agent, or Firm*—Kerkam, Stowell, Kondracki & Clarke

[57] ABSTRACT

A catheter arrangement and associated method provides for the application of a cell treatment agent, such as genetic material or drugs to be inserted within the cells of a patient in vivo. The catheter arrangement uses an optical fiber having a prism at its tip. Laser energy from the optical fiber is directed by the prism through a window portion on a side of the catheter. The window portion has a plurality of holes so as to divide the laser energy into a plurality of microbeams. The microbeams potate cell walls of the patient's cells. A treatment agent channel in the catheter allows the treatment agent to be provided directly to the same holes through which the microbeams pass such that the treatment agent is very efficiently applied to the porations in the cell walls.

24 Claims, 2 Drawing Sheets

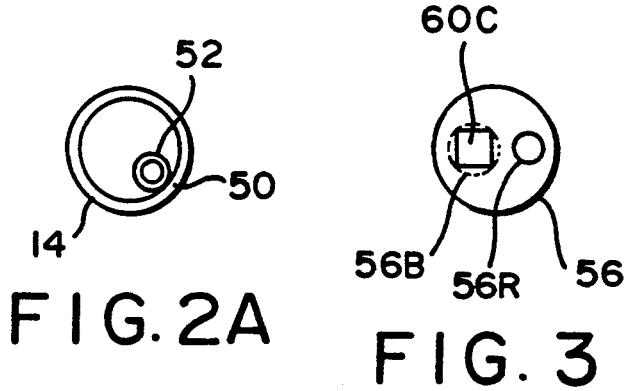
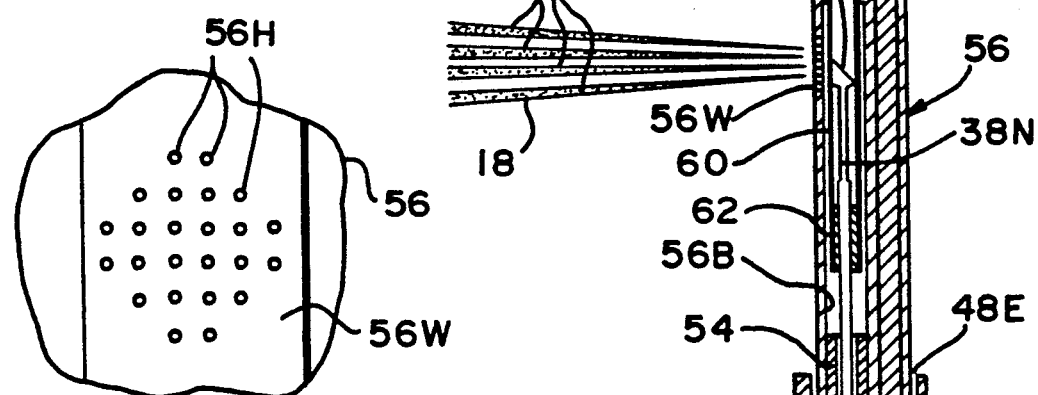
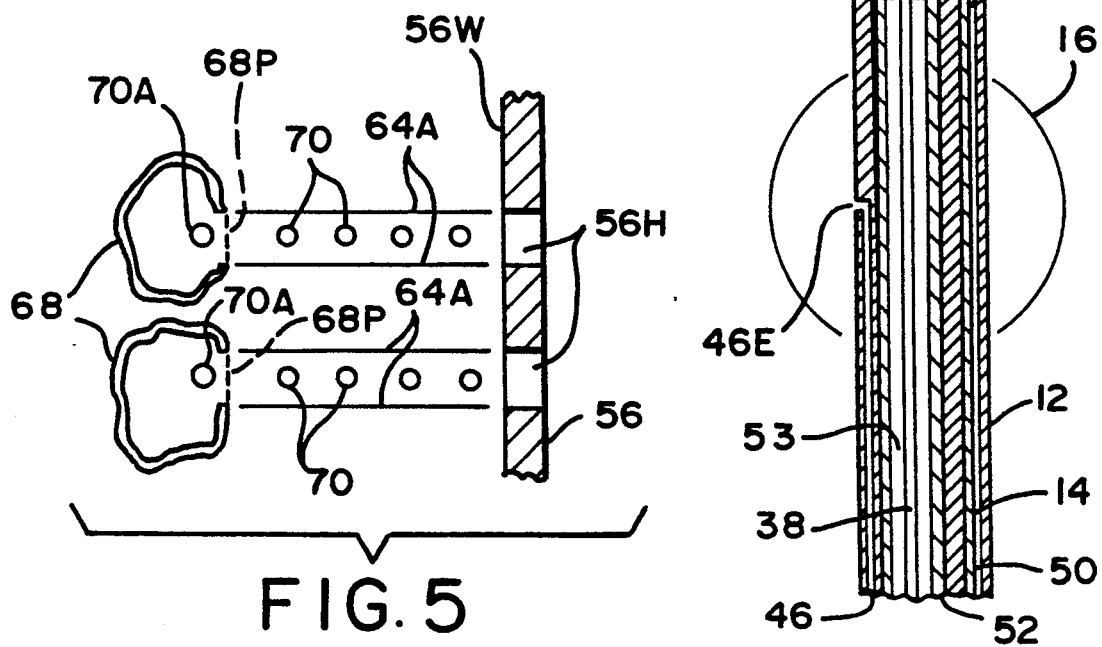

CELL TREATMENT APPARATUS AND METHOD

This is a continuation of application Ser. No. 07/866,473, filed Apr. 10, 1992.

BACKGROUND OF THE INVENTION

This invention relates to a cell treatment apparatus and method. More specifically, this invention relates to a treatment apparatus and method using at least one laser beam to porate (create a pore or poration) in a patient's cells in vivo.

Various techniques have been used, at least experimentally, for transfection of cells (i.e., insertion of new genetic material into the DNA structure of cells).

One technique for transfection of cells has used laser poration. This approach has been performed in vitro using a laser beam to porate a single cell at a time under a specially adapted microscope. The microscope allows the direct puncture of the cell membrane in the presence of the gene. Specifically, an operator directs the laser beam towards an individual cell and the puncture of the cell membrane allows genetic material on the same slide as the cell to enter into the cell. This approach is labor intensive and not practical to use in vivo. This laser poration technique is described in the article by Tao et al. entitled "Direct Gene Transfer Into Human Cultured Cells Facilitated By Laser Micropuncture of Cell Membrane" in the Proceedings of the National Academy of Science in 1987; 84:4180–4184.

Other approaches to transfection of cells have included chemical methods or electrical poration used in a cell culture, but such methods are not readily applicable in vivo. In other words, such methods may allow treatment of cells which have been removed from the patient, but do not allow treatment of cells remaining with the patient (human or animal).

The Nabel et al. article entitled "Site-Specific Gene Expression in Vivo by Direct Gene Transfer Into the Arterial Wall" in Science in 1990; 249(4974):1285–1288 discloses a technique for transfecting genes in vivo which has been used in the arteries of pigs. This technique uses a catheter with a dual balloon system at the tip of the catheter. The two balloons are inflated to create a temporary chamber which allows the exposure of the arterial wall to a viral transporting agent in solution. This has been used successfully to transfect the arterial wall with a DNA-plasmid having a viral carrier. However, this double balloon method requires 30 minutes to bathe the arterial wall with the DNA-plasmid to be effective. This is not feasible in certain applications such as in the coronary circulation. Moreover, the time required for such a technique to work may pose severe problems even at other locations within the arteries of an animal or human.

The Lim et al. article entitled "Direct In Vivo Gene Transfer Into the Coronary and Peripheral Vasculatures of the Intact Dog" appearing in Circulation, volume 83, no. 6, June 1991, pages 2007-2011, discloses a technique where endothelial cells are removed from the test animal and then transfected prior to reintroduction into the animal. In addition to that in vitro technique, the article describes in vivo transfection of arteries of dogs using catheters placed in peripheral vessels of the dogs. Proximal and distal lumens of the vessels were occluded with removable ligatures. In somewhat similar fashion to the dual balloon system, a temporary chamber is established and a transfection solution is supplied into that temporary chamber within the vessels of the animal. The article describes allowing the transfection solution to remain in the vessel for one hour.

Apart from the problems in developing medically effective techniques for using cell transfection, medical techniques for applying drugs to a patient have encountered problems. Specifically, a drug must be given in sufficient dosage that it will have the desired effect when a portion of it reaches the area of the body which the drug is supposed to treat. However, the dosage must not be so high that the portion of the drug which reaches other parts of the body causes unacceptable side effects. In other words, it has been difficult to introduce a drug into a patient without having significant portions of the drug reach portions of the body other than the portion where one wanted the drug to act. If one lowers the dosage of the drug, it may fail to reach the desired location within the body in sufficient quantity to have the desired effect. However, if one raises the dosage, the unintended consequences of the drug may increase in magnitude.

Various techniques have been developed to cause drugs to concentrate within a certain desired site of the body of a patient. Although such techniques have been quite useful, they still fail to give the desired control over the application of drugs that is necessary or desirable for certain conditions and circumstances.

OBJECTS AND SUMMARY OF THE INVENTION

Accordingly, it is a primary object of the present invention to provide a new and improved cell treatment apparatus and method.

A more specific object of the present invention is to provide for highly efficient cell treatment in vivo.

A further object of the present invention is to provide for transfection of cells in vivo relatively quickly (i.e., the cells in vivo need not be exposed for such long periods that lengthy disruptions, such as blocking of artery flow, are required).

Yet another object of the present invention is to provide for the efficient application of drugs to a patient.

The above and other objects which will become more apparent as the description proceeds are realized by an apparatus for patient treatment having a laser catheter. The laser catheter includes an optical fiber, a body having a wall with a window portion disposed therein to pass laser energy from the optical fiber, and a treatment agent channel inside the body. The window portion passes laser energy in the form of a plurality of distinct beams. There are at least three distinct beams each of which passes out of the window portion with a width of less than 200 microns for poration of a patient's cells in vivo. (As used herein, the width will be the largest cross-sectional dimension of a beam at a particular location, specifically where it passes out of the window portion.) The treatment agent channel is operable to supply treatment agent to a location for entry into a patient's cells in vivo after the patient's cells have been porated by the plurality of distinct beams.

Preferably, the plurality of distinct beams includes at least three beams which pass through the window portion in the same general direction. (As used herein, the three beams would be in the same general direction if each beam is within 30 degrees of the other two beams.) The window portion has a plurality of openings, each opening corresponding on a one-to-one basis with one beam of the plurality of distinct beams. Each of the openings has a width of less than 100 microns. More generally, the window portion has an opening through which laser energy may pass and the treatment agent channel is connected to the opening for supplying treatment agent by way of the opening for pressurized flow towards a patient's cells for entry therein after the patient's cells have been porated by the laser energy.

The apparatus may further include a flushing solution catheter connected to the laser catheter and having a flushing solution channel terminating in a flushing solution exit for applying flushing solution to a treatment site in a patient. The flushing solution catheter includes a balloon mounted thereon and a balloon channel connected to the balloon for controlling (inflating and deflating) the balloon. The window portion is on a side of the body. The treatment agent channel is connected to the openings for supplying treatment agent by way of the openings for pressurized flow towards a patient's cells for entry therein after the patient's cells have been porated by the laser energy.

The present invention may alternately be described as an apparatus for patient treatment including a treatment catheter which has an optical fiber, a body having a wall with a window portion disposed therein to pass laser energy from the optical fiber, and a treatment agent channel inside the body. The window portion passes laser energy for poration of a patient's cells in vivo. The treatment agent channel is operable to supply treatment agent to a location for entry into the patient's cells. The treatment catheter further includes a flushing solution channel terminating in a flushing solution exit for applying flushing solution to a treatment site in a patient.

The window portion passes laser energy in a plurality of distinct beams having a width of less than 100 microns.

The present invention may alternately be described as an apparatus having a treatment catheter including an optical fiber, a body having a wall with a window portion disposed therein to pass laser energy from the optical fiber, and a treatment agent channel inside the body. The window portion passes laser energy in a form including at least one beam having a width of less than 200 microns passing through an opening of less than 200 microns in the window channel portion. The treatment agent channel is disposed to supply treatment agent by way of the opening to a location for entry into a patient's cells after poration. The treatment catheter may further include a balloon mounted thereon and a balloon channel connected to the balloon for inflating the balloon. The window portion is on a side of the body. The treatment catheter includes a laser catheter having the optical fiber, body, and treatment agent channel and a flushing solution catheter as described above.

The method of the present invention may be described as a method of treating cells of a patient in vivo. Laser energy is applied to the cells of the patient in vivo to cause porations in the cells. A treatment agent is then applied to the cells having porations therein such that the treatment agent enters the cells through the porations.

In one technique, the treatment agent includes genetic material and the applying of the treatment agent causes the cells to be transfected. In an alternate technique, the treatment agent is a drug.

The laser energy is applied by application of a plurality of distinct beams, different ones of the beams being applied to different cells at the same time. The method further includes the step of inserting a laser catheter into a patient and the beams are applied to the cells after leaving the laser catheter with a width of less than 200 microns. The beams leave the laser catheter more preferably with a width of less than 100 microns and there are at least 12 of the beams which exit through openings on a side of the laser catheter. The treatment agent is forced out the openings to follow multiple paths corresponding to the beams.

The laser energy exits from the laser catheter from at least one opening and the treatment agent is forced out that opening to follow at least one path corresponding to a beam of the laser energy.

The method of the present invention may alternately be described as a method of treating cells of a patient in vivo by inserting a laser catheter into the patient, applying laser energy to the cells of the patient in vivo to cause porations in the cells, and applying a treatment agent to the cells having porations therein such that the treatment agent enters the cells through the porations. The laser energy exits from at least one opening in the laser catheter and the treatment agent is forced out the opening to follow at least one path corresponding to a beam of the laser energy. The inserting step involves insertion of the laser catheter into an artery of the patient.

BRIEF DESCRIPTION OF THE DRAWINGS

The above and other features of the present invention will be more readily understood when the following detailed description is considered in conjunction with the accompanying drawings wherein like characters represent like parts throughout the several views and in which:

FIG. 2 shows a side view, with parts in cross section, of the treatment catheter or catheter assembly of FIG. 1;

FIG. 2A shows a simplified end view of the laser catheter;

FIG. 3 shows an end view of a tip of the arrangement of FIG. 2;

FIG. 4 shows a screen or window portion used to provide a plurality of very small beams of laser energy from a single larger beam of laser energy; and FIG. 5 shows a schematic view of a laser beam and genetic code material being applied to different cells.

DETAILED DESCRIPTION

Figure 1:
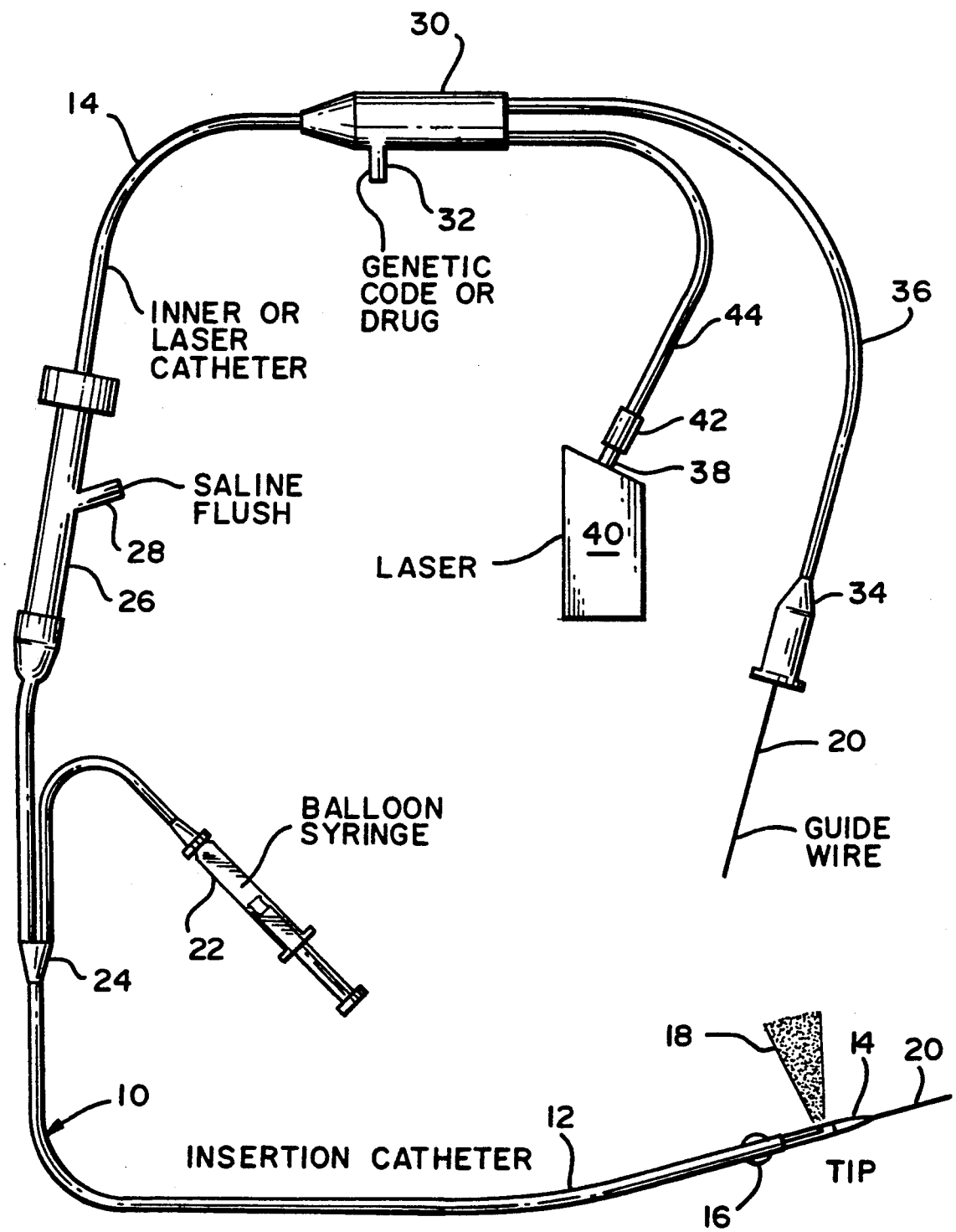
FIG. 1 shows a side view of a treatment catheter arrangement according to the present invention.

Turning initially to FIG. 1, a brief overview of the preferred embodiment of the present invention will be given. A treatment catheter 10, which might also be called a catheter assembly, includes an insertion catheter 12 and a laser catheter 14. The insertion catheter 12 has a balloon 16 mounted thereon for blocking blood flow in an artery, while the laser catheter 14 is applying laser energy 18 to porate cells (not shown) at the same time as genetic code material (not separately shown) is proceeding along the same paths as the laser energy 18. A guide wire 20 is used to guide the catheters to their intended location such that the laser energy 18 and associated genetic material may be applied to the proper site within the patient.

A balloon syringe 22 controls the balloon 16 in known fashion by way of a Y connection 24, which may be constructed in known fashion. Saline or other flush may be provided to the insertion catheter 12 by way of Y connector 26 having entry tube 28 for those purposes. The laser or inner catheter 14 is visible as it extends out the back of connector 26 towards the Y connector 30 having tube 32 for entry of genetic material or a drug to be inserted in the patient. A pump (not shown) or other arrangement may be connected to tube 32 to supply genetic material or a drug under pressure to inner catheter 14. The Y connector 30 is constructed in known fashion to merge the guide wire 20 (which proceeds from the luer lock or hemostatic Y-connector 34 and tube 36), optical fiber 38 (operably connected to laser 40 and proceeding through fiber connector 42 and tube 44), and the material inserted into the entry tube 32. Accordingly, the inner or laser catheter 14 proceeding out the left side of connector 30 includes the guide wire 20, the optical fiber 38, and any material supplied to the tube 32.

Turning now to FIG. 2, the details of the tip of the catheter arrangement of FIG. 1 will be explained. The insertion of flush catheter 12, which may be made of a common catheter material such as Teflon type material, is generally a hollow cylinder having a balloon control channel 46 separated from the main hollow part of the tubular catheter 12 and used to control the balloon 16 in known fashion by way of an exit 46E for the channel 46. A flushing solution channel 48, which is separate and distinct from the balloon channel 46, is disposed within the main hollow part of catheter 12. More specifically, the channel 48 may extend circumferentially in a ring just inside the wall of catheter 12 and outside of the inner or laser catheter 14. The channel 48 proceeds to a circumferential flush exit 48E.

The inner or laser catheter 14 has a generally cylindrical tube 50 of common flexible material used for catheters. Inside of the tube 50 is a guide wire tube 52 for slidably receiving the guide wire 20 therein. The tube 52, would be secured to one side of the tube 50 as best understood by momentarily turning to the end view of laser catheter 14 in FIG. 2A. Instead of having the tube 52 be distinct from tube 50, tube 52 might simply be a lengthwise extending pocket in tube 50 extruded at the same time as tube 50.

Turning back to FIG. 2, the optical fiber 38 extends inside of tube 50 and outside of tube 52 and extends into a connecting tube 54, which is preferably about 4 millimeters long and made of metal. The guide wire tube 52 and the connecting tube 54 would be glued, have barbs (not shown) to grip tube 50, or otherwise fixed in position (possibly simply by friction) within the tube 50. The connecting tube 54 secures a tip 56 to the tube 50. Specifically, the connecting tube 54 may be glued, friction-fit, snap fit using a ledge ring (not shown), or otherwise fixed to a cylindrical bore 56B within the tip 56. A second bore or cylindrical hole 56R (turn momentarily to FIG. 3) extends lengthwise in the tip 56. The tip 56, which is preferably made of surgical steel and is 8.7 millimeters long in the preferred embodiment, has a tapered end 58 which may be made of Teflon or other surgical materials commonly used in catheters. The tapered portion 58 would be hollow or otherwise allow for passage of guide wire 20 therethrough.

The optical fiber 38 proceeds through connecting tube 54 to a glass hood 60. The optical fiber 38 is secured to the glass hood 60 by way of epoxy 62 applied after heating and creating a vacuum within the hood 60. The hood 60 preferably has a square cross section to fit within a square cross section cavity 60C (also refer momentarily to FIG. 3) which extends out from the circular bore or cavity 56B. Accordingly, the glass hood 60 may be adhered, friction-fit, or otherwise fixed within cavity 60C to prevent relative angular movement between the optical fiber 38 and the tip 56. The optical fiber 38 may have a portion of its cladding removed at its narrow portion 38N adjacent its end. The optical fiber 38 has a tip 38T to cause any laser beam to be directed sideways out a window portion 56W in the side of the wall of tip 56. More details of the construction of tip 38T and glass hood 60 may be obtained from U.S. Pat. No. 5,061,265, invented by the present inventor together with Stephan E. Friedl, issued on Oct. 29, 1991, and hereby incorporated by reference. Generally, the tip 38T is made into a prism using techniques described in that prior patent so as to deflect all, or substantially all, of the laser energy out the window portion 56W.

Continuing to view FIG. 2, but also referring to the enlarged view of the window portion 56W of tip 56 appearing in FIG. 4, the window portion 56W is essentially a laser screen having a plurality of very small holes 56H through which laser micro-beams 64 may pass. The holes 56H would be distributed throughout an area of between one square millimeter and three square millimeters. Preferably, the holes are distributed evenly over a circular area of two square millimeters which would correspond to the width of the beam exiting from the tip 38T. Each of the holes 56H would be less than 200 microns. More specifically, the holes would be below 100 microns in diameter such that the microbeams 64 would have a corresponding width as they leave the tip 56 of catheter 14. Most specifically, the holes would be 50 to 100 microns in diameter to provide beams of the same size. The holes 56H may be made by using an excimer laser or electrodischarge machine. The microbeams 64 would preferably have a diameter of 50 to 75 microns. As apparent from FIGS. 2 and 4, there are at least three beams which go in the same general direction. More specifically, at least 12 beams, corresponding to at least 12 holes, proceed out one side of the tip 56. As will be appreciated, there is a one-to-one correspondence between the beams 64 and the holes 56H. The beams 64 are distinct (i.e., meaning distinct where they leave the tip 56), but each of the beams 64 diverges somewhat because of the properties of the prism tip 38T of the optical fiber 38.

The openings 56H also allow passage of treatment agent which is supplied via treatment agent channel 53 (FIG. 2) in between fiber 38 and tube 50, connecting tube 54 (i.e., between tube 54 and fiber 38) and bore 56B.

Operation

Having described the structural features of the present invention, the method according to the present invention will now be described.

Although the present invention has applicability to providing treatment very efficiently on a cellular level at various sites on a patient's body or in a patient's body, the specifics of the structure which has been described is best suited for applying treatment to the walls of an artery and the explanation which follows will emphasize such an application of the invention.

A patient having an artery, such as a coronary artery, with atherosclerotic plaque is appropriately sedated and placed upon a x-ray or fluoroscopic table. Various know steps could be used for locating the tip 56 of laser catheter 14 at the site for treatment of the patient's artery and only a basic discussion of the procedure for locating the tip 56 at the proper site will be presented herein. Initially, the guide wire 20 and a guide catheter of common design (not shown) would be inserted into the patient using an introducer sheath of common design (not shown). The guide catheter would extend to the mouth of the artery, whereas the guide wire 20 would be manipulated to anchor its end just beyond the partial obstruction caused by the plaque.

The treatment catheter 10 (refer to FIG. 1), which includes both the laser or inner catheter 14 and the insertion or flush catheter 12 would then be slid along the guide wire 20. The catheters 12 and 14 would move along the guide catheter (not shown) in known fashion until the balloon 16 of the insertion catheter 12 is outside of the guide catheter and until the window portion 56W is adjacent the portion of the artery for which treatment is intended. The laser catheter 14 would be rotated until its window portion 56W (refer to FIG. 2) faces the side of the artery wall which is to be treated. The balloon 16 is then inflated using the balloon syringe 22 such that the part of the artery downstream (it would correspond to the rightward direction in FIG. 1) of balloon 16 is blocked from receiving further blood. The balloon 16 may be used to block the blood flow for up to about 60 seconds. The blockage would normally not need to be maintained for 60 seconds, but the surgeon would be using his professional judgement as to how long the blockage might be tolerated for a particular individual. At any rate, the blockage would be less than two minutes at a time and is significantly less than the blockage times required for the double balloon prior art technique described in the background portion of this application. If advisable, the balloon could be deflated and re-inflated to provide repeated treatments without maintaining the blockage for longer than about 60 seconds each time.

After the balloon 16 has been inflated and now considering FIGS. 1 and 2, a saline or other flushing solution is supplied to connector 26. The saline travels along the flushing solution channel 48 and exits from 48E (see especially FIG. 2) so as to clean out blood in the portion of the artery just downstream from the balloon 16. After this space has been flushed with saline, the saline flush is halted and the laser 40 is activated to generate the laser energy 18 (FIG. 1) in the form of the microbeams 64 (FIG. 2). The laser 40 would preferably be a pulsed laser pulsed at one to five times a second, such as a 355 nanometer tripled YAG or a flash lamp excited dye laser at 504 nanometers. However, a continuous wave argon laser or other type of laser might be used. A treatment agent will be supplied to the cells which are porated by the laser microbeams. A treatment agent as used herein is a cell treatment agent, meaning that it has medicinal effect (might include killing the cell if that was medically helpful) or harmful effect (if desirable for testing purposes) or remedial effect when placed within a cell after passing through potations caused by the laser microbeams. The treatment agent, such as genetic material or a drug is supplied to the connector 30 (FIG. 1) and passes through the treatment agent channel 53 and through the space between optical fiber 38 and connecting tube 54 into the hole or bore 56B for passage as a high pressure stream out of the window portion 56W. Referring now to FIG. 5, two cells 68 are shown having porations 68P therein as caused by the laser microbeams 64 having edges 64A shown in FIG. 5, the microbeams having passed out of holes 56H. Also passing out of the holes 56H is a high pressure solution containing the treatment agent 70 disposed therein and some of the treatment agent 70A has entered into the cells 68 by way of the potations 68P. If the agent 70 includes genetic materials, the solution may be culture material such as DMEM (Dulbecco's Modified Eagle's Medium) or normal saline. Quite importantly, the treatment agent 70 passes out of the same holes as the beams 64 such that the treatment agent passes along the same paths as the various microbeams 64. Accordingly, the genetic material should enter through the potations 68P in the cell walls of cells 68. In other words, the treatment agent is concentrated precisely where it is most likely to be effective. Significantly, the beam width is smaller than the size (i.e., longest dimension) of the cell and would also preferably be smaller than the normal dimension of the cell (i.e., the dimension of the cell extending perpendicular to the direction of the beam).

It should be appreciated that some of the microbeams 64 may hit the nucleus of a cell and kill the cell. Others of the microbeams may hit the edge of a cell without providing a useful potation. However, using a large number of the microbeams should allow for treatment, on a cellular level, of a sufficient number of cells that benefits will be obtained.

As an alternative to the simultaneous spraying of treatment agent 70 out of the holes 56H while the beams 64 are passing out of the holes, one might porate the cells 68 by application of the beams 64 and, immediately after turning off the beams 64, spray the treatment agent 70 out of the holes 56H. Since the potations 68P will close relatively quickly, the treatment agent should be sprayed immediately after turn off of the beams.

If one is simply treating a single part of the artery wall, one might line up the window portion 56W to face the proper direction by use of a marker (not shown) on part of the laser catheter 14. For example, a hole or pattern (not shown) might be placed on the side of steel tip 56 opposite to the window portion 56W. The surgeon would then observe the marker by use of the x-ray table and rotate the laser catheter 14 until the marker was opposite to the part of the artery wall which was to be treated. If desired, two markers of different configuration might be used to provide more information to the surgeon and to help better line up the window portion 56W such that it faces the part of the artery wall which is to be treated. Instead of placing the markers on the steel tip 56, the markers might alternately be placed upon the tapered portion 58 (which is made of plastic) and/or the outer surface of the laser catheter 14. If desired, one may treat the artery wall in a complete circumference. One may apply laser energy and treatment agent (either simultaneously or treatment agent immediately after laser as discussed above) with the laser catheter 14 disposed in one angular position. The laser would then be turned off, the laser catheter 14 would be rotated to a different angular position and the laser and treatment agent application would be repeated. The laser would be turned off and the laser catheter 14 would be rotated to another angular position for treatment. This process of rotation treatment followed by further rotation and treatment may be performed around the complete circumference of a portion of the artery. Additionally, or alternately, one may move the laser catheter 14 along the guide wire 20 to a different place within the artery before applying further treatment. In other words, if the blockage or other problem in the artery extends significantly in a lengthwise direction, treatments may be applied at different places along the length of the blockage.

Advantageously, a vacuum may be applied to tube 28 to remove genetic material or drug remaining free after laser operation and before deflating balloon 16. This reduces the amount of material going down stream.

After application of the laser beams and treatment agent has been completed, the balloon 16 would be deflated so as to reopen the artery. The treatment catheter 10 composed of laser catheter 14 and insertion catheter 12, is then removed from the patient. The guide catheter and guide wire would be removed from the patient and normal post-operative procedures would be followed such as checking the patient to insure that no artery walls were punctured.

Having shown how the present invention may be used to very efficiently provide treatment at a cellular level by injecting cell treatment agents 70 directly into cells 68 as illustrated in FIG. 5, some specific examples of such treatments will now be presented. Generally, any genetic code material, such as DNA plasmids, and any drug applicable for cellular treatment could be used.

EXAMPLE 1

A patient has a buildup of plaque on the walls of a coronary artery. The treatment catheter 10 would be inserted into the patient under the procedure explained above and the microbeams 64 are used to porate smooth muscle cells of the artery walls. The treatment agent would be plasmids of DNA which encode antisense gene. The gene may be under the control of mouse metallothionein promotor. A virus carrier would be used in known fashion to allow the desired genetic material to enter the nucleus of the cells into which the treatment agent is inserted. The antisense genetic code will fool the smooth muscle cells to inhibit growth patterns which cause the blockage of arteries.

EXAMPLE 2

A patient has a buildup of plaque on the coronary arteries. The treatment catheter 10 would be inserted into the patient under the procedure described above and the microbeams 64 are used to porate the endothelial cells of the artery walls. The treatment agent would be plasmids of DNA which encode a tissue plasminogen activator gene under the control of the mouse promotor as with example 1 and having a virus carrier. The human plasminogen activator would cause the production of enzymes which reduce formation of clots.

EXAMPLE 3

A patient has a malignant tumor in the colon. The patient would be sedated and a colonoscopy would be performed. Instead of using an x-ray or fluoroscopic table to locate the position of the treatment device placed within the patient, the treatment device (not shown) may include an optical fiber to allow the surgeon to see within the colon. The probe or medical device inserted into the patient would include a laser catheter similar to catheter 14 of FIG. 2. Upon the window portion (similar to 56W of FIG. 2) being lined up to face the tumor, laser energy is applied to provide microbeams which potate the cells of the tumor and a cancer agent, such as 5-fluorouracil or donarubicin, is injected out the same plurality of holes used for generating the microbeams. Saline or other solution may be used to carry the cancer agent drug to the cells. The cancer agent would enter into numerous of the cancer cells and kill them. Advantageously, the poration of the cells by the laser beam improves the efficiency of application of the cancer agent to the cells. A smaller portion of the cancer agent harms adjacent healthy cells than would be the case if one simply applied the cancer agent against cells which had not been porated. Some of the cancer cells may be killed simply by application of the laser beam, but the inclusion of the cancer agent helps to kill a greater portion of the cancer cells than would otherwise be the case. Additionally, if one simply relied upon the laser to kill cancer cells, one might have to use a higher laser power which in turn might damage healthy cells behind or adjacent to the cancer cells.

EXAMPLE 4

The patient would be the same as in example 2 and the same procedure would be followed except that the treatment agent is the drug heparin carried by saline or other solution. The drug prevents formation of clots.

EXAMPLE 5

An animal may be used to test various anti-plaque techniques by using the present invention to induce plaque in walls of arteries. The treatment catheter 10 is used to porate endothelial cells on artery walls of the animal (patient) for introducing a plasmid of DNA which encodes for human growth hormone gene under the control of a mouse metallothionein promoter. A viral carrier would be used in known fashion to allow the desired genetic material to enter the nucleus of the cells into which the treatment agent is inserted. The expression of growth hormone in transfected cells will then result in the expression of various cellular proteins causing cell growth which could be responsible in part for the development of plaque in the arterial wall. This information could then be used to develop either drugs or other methods to inhibit gene expression in order to block this growth.

Although specific constructions and examples have been presented herein, it is to be understood that these are for illustrative purposes only. Various modifications and adaptations will be apparent to those of skill in the art. For example, one might use a double balloon catheter with the laser beams and treatment agents being applied from a window portion in between two balloons. Although the present invention has the highly advantageous feature of injecting the treatment agents out the same holes as the laser beams, the present invention, in its broadest aspects, might include a double balloon arrangement wherein the treatment agent comes out holes separate from the laser beams and fills the chamber established between the two balloons blocking part of an artery. Since the laser beams would be porating the cells within artery walls between two such balloons, the treatment agent, such as genetic material, could transfect the cells more quickly than in the prior art double balloon technique discussed in the background portion of this application since that prior art technique did not provide for cell porations. Such a double balloon technique may also use known dye materials inserted to enhance absorption of laser energy. Such materials are disclosed in the present inventors' prior U.S. Pat. Nos. 4,860,743 and 5,041,109 issued respectively on Aug. 29, 1989 and Aug. 20, 1991 and hereby incorporated by reference. Although the laser 40 would preferably be a pulsed type laser, one might use a thermocouple to guard against overheating if the laser 40 was a continuous wave laser. In view of these and other possible modifications, it will be appreciated that the scope of the present invention should be determined by reference to the claims appended hereto.

What is claimed is:

1. An apparatus for patient treatment comprising: a treatment catheter including an optical fiber, a body having a wall with a window means disposed therein to pass laser energy from said optical fiber, and a treatment agent channel inside said body, said window means passing laser energy for poration of a patient's cells in vivo, said treatment agent channel operable to supply treatment agent to said window means for entry into a patient's cells in vivo after the patient's cells have been porated by said laser energy, said treatment catheter further including a flushing solution channel distinct from said treatment agent channel and terminating in a flushing solution exit for applying flushing solution to a treatment site in a patient.

2. The apparatus of claim 1 wherein said window means has an opening through which laser energy may pass and wherein said treatment agent channel is connected to said opening for supplying treatment agent by way of said opening for pressurized flow towards a patient's cells for entry therein after the patient's cells have been porated by said laser energy.

3. The apparatus of claim 1 wherein said window means passes laser energy in a plurality of distinct beams, each of which has a width of less than 100 microns.

4. The apparatus of claim 1 wherein said window means has a plurality of openings, each opening corresponding on a one-to-one basis with one beam of a plurality of distinct beams in which said laser energy is disposed.

5. The apparatus of claim 4 wherein said treatment agent channel is connected to said openings for supplying treatment agent by way of said openings for pressurized flow towards a patient's cells for entry therein after the patient's cells have been porated by said laser energy.

6. The apparatus of claim 5 wherein said treatment catheter includes a balloon mounted thereon and a balloon channel connected to said balloon for inflating said balloon, said window portion is on a side of said body, and wherein said window portion passes laser energy in a plurality of distinct beams, each having a width of less than 100 microns.

7. An apparatus for patient treatment comprising: a treatment catheter including an optical fiber, a body having a wall with a window means disposed therein to pass laser energy from said optical fiber, and a treatment agent channel inside said body, said window means passing laser energy in a form including at least one beam passing through an opening of less than 200 microns in said window portion, said opening functioning to limit said at least one beam in diameter, said treatment agent channel disposed to supply treatment agent by way of said opening to a location for entry into a patient's cells in vivo after the patient's cells have been porated by said laser energy.

8. The apparatus of claim 7 wherein said treatment catheter includes a balloon mounted thereon and a balloon channel connected to said balloon for inflating said balloon and said window means is on a side of said body.

9. The apparatus of claim 8 wherein said window means has a plurality of openings, each opening corresponding to a one-to-one basis with one beam of a plurality of distinct beam in which said laser energy is disposed, and each opening connected to said treatment agent channel is connected to said openings for supplying treatment agent by way of said openings for pressurized flow towards a patient's cells for entry therein after the patient's cells have been porated by said laser energy.

10. The apparatus of claim 8 wherein said treatment catheter includes a laser catheter having said optical fiber, said body and said treatment agent channel and a flushing solution catheter connected to said laser catheter and having a flushing solution channel terminating in a flushing solution exit for applying flushing solution to a treatment site in a patient.

11. The apparatus of claim 7 wherein said at least one beam has a width of less than 100 microns and said opening is less than 100 microns across.

12. An apparatus for patient treatment comprising: a laser catheter including an optical fiber, a body having a wall with a window means disposed therein to pass laser energy from said optical fiber, and a treatment agent channel inside said body, said window means passing laser energy in the form of a plurality of distinct beams, there being at least three distinct beams, each of the three beams passes out of said window portion in the same general direction for poration of a patient's cells in vivo, said treatment agent channel operable to supply treatment agent to a location for entry into a patient's cells in vivo after the patient's cells have been porated by said plurality of distinct beams.

13. The apparatus of claim 12 wherein said treatment catheter includes a balloon mounted thereon and a balloon channel connected to said balloon for inflating said balloon and said window means is on a side of said body.

14. The apparatus of claim 12 wherein said window means has a plurality of openings, each opening corresponding on a one-to-one basis with one beam of a plurality of distinct beams in which said laser energy is disposed and wherein said treatment agent channel is connected to said openings for supplying treatment agent by way of said openings for pressurized flow towards a patient's cells for entry therein after the patient's cells have been porated by said laser energy.

15. The apparatus of claim 14 further comprising a flushing solution catheter connected to said laser catheter and having a flushing solution channel terminating in a flushing solution exit for applying flushing solution to a treatment site in a patient.

16. A method of treating cells of a patient in vivo comprising the steps of:
    inserting a laser catheter into the patient;
    passing laser energy through an opening at a distal end of said catheter such that the laser energy is applied to the cells of the patient in vivo to cause porations in the cells; and
    applying a treatment agent to the cells having porations therein such that the treatment agent enters the cells through the porations said applying of the treatment agent being performed by forcing the treatment agent out said opening to follow at least one path corresponding to a beam of said laser energy.

17. The method of claim 16 wherein the treatment agent includes a DNA plasmid and the applying of the treatment agent causes the cells to be transfected.

18. The method of claim 17 wherein the step of applying laser energy uses application of laser energy in the form of a plurality of distinct beams, different ones of the beams are applied to different cells at the same time.

19. The method of claim 18 and wherein said beams are applied to the cells after leaving said laser catheter with a width of less than 200 microns.

20. The method of claim 19 wherein said beams leave said laser catheter with a width of less than 100 microns and wherein there are at least 12 of said beam which exit through openings on a side of said laser catheter.

21. The method of claim 19 wherein said laser beams exit from openings on a side of said catheter and said treatment agent is forced out said openings to follow multiple paths corresponding to said beams.

22. A method of treating cells of a patient in vivo comprising the steps of:
   applying laser energy to the cells of the patient in vivo to cause porations in the cells; and
   applying a treatment agent to the cells having porations therein such that the treatment agent enters the cells through the porations; and
further comprising the step of inserting a laser catheter into the patient and wherein the laser energy is applied to the cells as a plurality of beams each leaving said laser catheter with a width of less than 200 microns and wherein the treatment agent is a drug.

23. A method of treating cells of a patient in vivo comprising the steps of:
   inserting a laser catheter into the patient; applying laser energy to the cells of the patient in vivo to cause porations in the cells, the laser energy exiting from at least one opening in said laser catheter; and
   applying a treatment agent to the cells having porations therein such that the treatment agent enters the cells through the porations; and
wherein said treatment agent is forced out said opening to follow at least one path corresponding to a beam of said laser energy.

24. The method of claim 23 wherein the inserting step involves insertion of the laser catheter into an artery of the patient.

* * * * *